US005717090A

United States Patent [19]
Bassler et al.

[11] Patent Number: 5,717,090
[45] Date of Patent: Feb. 10, 1998

[54] SIMULTANEOUS PREPARATION OF CAPROLACTAM AND HEXAMETHYLENEDIAMINE

[75] Inventors: Peter Bassler, Viernheim; Hermann Luyken, Ludwigshafen; Günther Achhammer, Mannheim; Tom Witzel, Ludwigshafen; Eberhard Fuchs, Frankenthal; Rolf Fischer, Heidelberg; Werner Schnurr, Herxheim, all of Germany

[73] Assignee: BASF Aktiengesellschaft, Ludwigshafen, Germany

[21] Appl. No.: 565,214

[22] Filed: Nov. 30, 1995

Related U.S. Application Data

[63] Continuation-in-part of Ser. No. 375,574, Jan. 18, 1995, abandoned.

[30] Foreign Application Priority Data

Jan. 5, 1995 [DE] Germany ............... 195 00 222.9

[51] Int. Cl.$^6$ ............................................. C07D 201/08
[52] U.S. Cl. .................. 540/539; 540/538; 564/492
[58] Field of Search ............... 564/492; 540/538, 540/539

[56] References Cited

U.S. PATENT DOCUMENTS 3,972,938   8/1976   Voges et al. ............... 564/492

*Primary Examiner*—Robert T. Bond
*Attorney, Agent, or Firm*—Keil & Weinkauf

[57] ABSTRACT

Caprolactam and hexamethylenediamine are prepared simultaneously starting from adiponitrile by a process in which (a) adiponitrile is partially hydrogenated to give a mixture containing essentially 6-aminocapronitrile, hexamethylenediamine, ammonia, adiponitrile and hexamethyleneimine, (b) the mixture obtained in (a) is subjected to a distillation to give ammonia as the top product and a bottom product I, (c) the bottom product I containing essentially 6-aminocapronitrile, hexamethylenediamine, adiponitrile, hexamethyleneimine, inert compound A and ammonia, the ammonia content being lower than that of the mixture used in stage (b), is subjected to a second distillation to give a mixture comprising the inert compound A and ammonia as the top product and a bottom product II, (d) the bottom product II is subjected, in a third column, to a distillation to give the inert compound A as the top product and a bottom product III, (e) the bottom product III is subjected, in a fourth column, to a distillation to give a top product KP1, containing essentially hexamethyleneimine and a bottom product IV, (f) the top product KP1 is subjected, in a fifth column, to a distillation to give a top product KP2, which contains essentially hexamethyleneimine, and (g) the bottom product IV containing essentially 6-aminocapronitrile and adiponitrile is subjected, in a sixth column, to a distillation to give 6-aminocapronitrile, and the 6-aminocapronitrile thus obtained is then cyclized to give caprolactam.

9 Claims, 1 Drawing Sheet

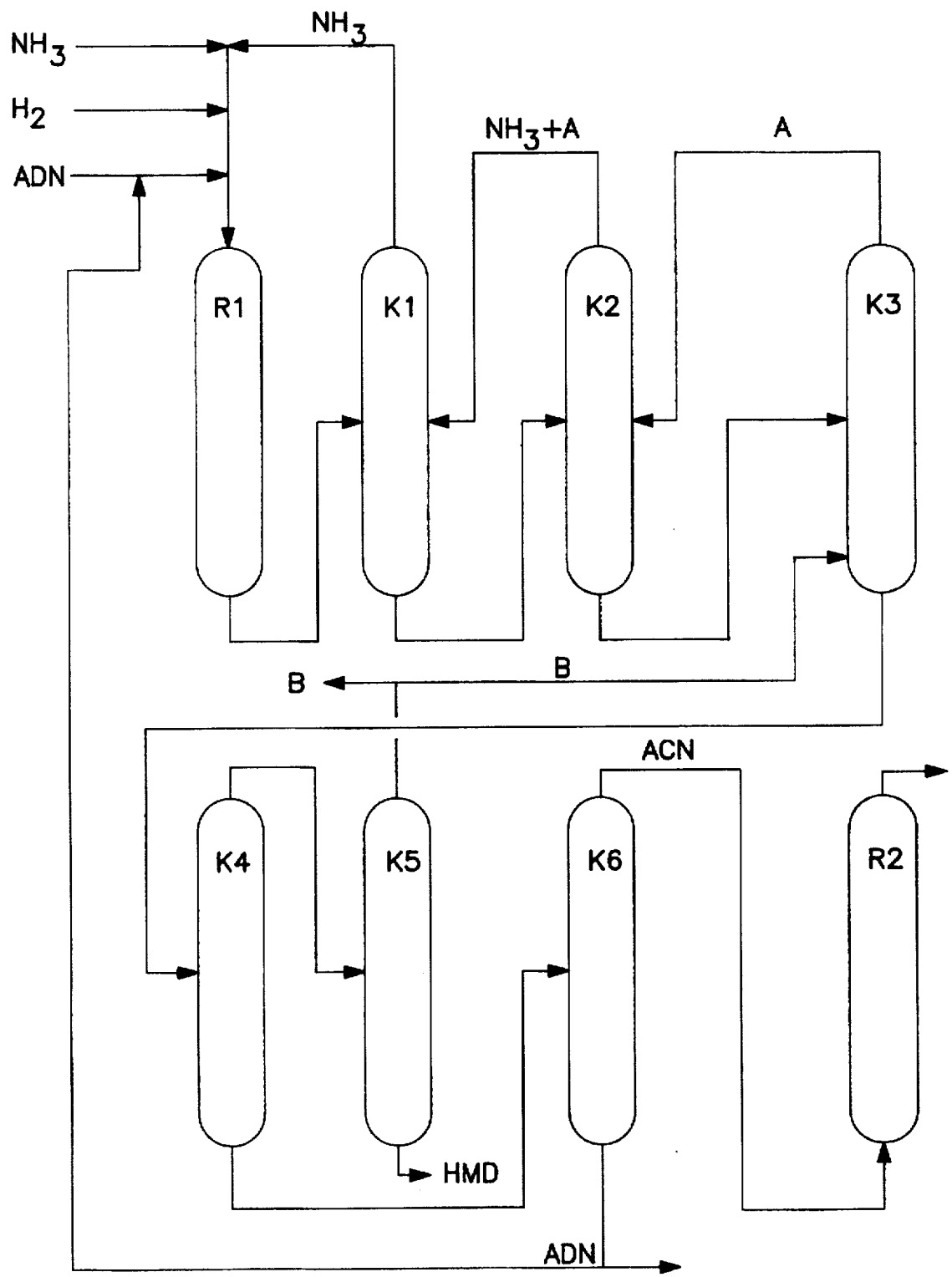

SIMULTANEOUS PREPARATION OF CAPROLACTAM AND HEXAMETHYLENEDIAMINE

This application is a continuation-in-part of application Ser. No. 08/375,574, filed on Jan. 18, 1995 now abandoned.

The present invention relates to a process for the simultaneous preparation of caprolactam and hexamethylenediamine starting from adiponitrile.

The present invention furthermore relates to an improved process for the simultaneous separation of 6-aminocapronitrile and hexamethylenediamine from a mixture containing these substances.

The partial hydrogenation of adiponitrile to 6-aminocapronitrile in the presence of ammonia and various catalysts has been sufficiently described. For example, U.S. Pat. No. 4,601,859 describes the use of catalysts based on rhodium on magensium [sic] oxide, U.S. Pat. No. 2,762,835 describes the use of Raney nickel, U.S. Pat. No. 2,208,598 describes the use of nickel on alumina, DE-A 848 654 describes fixed-bed catalysts based on copper/cobalt/zinc spinels and iron/cobalt spinels, DE-A 954 416 describes the use of cobalt on silica gel and DE-A 4 235 466 describes the use of iron sponges.

In the process described in WO 92/21650, aminocapronitrile yields of 60% at a conversion of 70% and hexamethylenediamine yields of 9% are obtained in the presence of Raney nickel. At a conversion rate of 80%, the yield is 62%.

It is also known that 6-aminocapronitrile can be reacted with water in the gas or liquid phase in the presence or absence of catalysts, with liberation of ammonia, to give caprolactam. For example, U.S. Pat. No. 2,301,964 describes a process in which from 10 to 25% strength solutions of 6-aminocapronitrile are converted in the liquid phase at from 250° to 290° C. into caprolactam in yields of up to 76%.

Furthermore, the cyclization of from 25 to 35% strength 6-aminocapronitrile solutions at 220° C. in the liquid phase in water with the addition of organic solvents in the presence of zinc compounds, copper compounds, lead compounds and mercury compounds is described in FR-A 2,029,540. Caprolactam yields of up to 83% are obtained here.

The cyclization of 6-aminocapronitrile can also be carried out in the gas phase (U.S. Pat. No. 2,357,484): starting from 80% strength aqueous solutions, caprolactam yields of 92% are obtained at 305° C. using alumina as catalyst.

EP-A 150 295 describes the conversion of 6-aminocapronitrile in the gas phase in the presence of copper/vanadium catalysts, hydrogen, water and ammonia at 290° C. with 77% yield of caprolactam.

Furthermore, DE-A 43 19 134 describes the conversion of 6-aminocapronitrile in water in the liquid phase, without the addition of a catalyst, to caprolactam.

A process for obtaining caprolactam via 6-aminocapronitrile starting from adiponitrile, in an overall process combining the two steps, is not evident from the abovementioned documents.

It is an object of the present invention to provide a process for the simultaneous preparation of caprolactam and hexamethylenediamine starting from adiponitrile. Furthermore, it is intended to provide a process which gives pure 6-aminocapronitrile and hexamethylenediamine in a continuous process from the reaction mixture obtained in the partial hydrogenation of adiponitrile, the 6-aminocapronitrile being cyclized in a further step to give to caprolactam. It is also intended as far as possible to reuse byproducts obtained in this process, preferably to recycle them to an earlier process stage.

We have found that this object is achieved by a process for the simultaneous preparation of caprolactam and hexamethylenediamine starting from adiponitrile, wherein (a) adiponitrile is partially hydrogenated to give a mixture containing essentially 6-aminocapronitrile, hexamethylenediamine, ammonia, adiponitrile and hexamethyleneimine, (b) the mixture obtained in (a) is subjected to a distillation to give ammonia as the top product and a bottom product I, the distillation being carried out at a bottom temperature of from 60° to 220° C. and a pressure of from 10 to 30 bar in the presence of a compound A which is inert under the distillation conditions and boils at from 60° to 220° C. at 18 bar, and the ammonia not being completely separated off, (c) the bottom product I containing essentially 6-aminocapronitrile, hexamethylenediamine, adiponitrile, hexamethyleneimine, inert compound A and ammonia, the ammonia content being lower than that of the mixture used in stage (b), is subjected to a second distillation to give a mixture comprising the inert compound A and ammonia as the top product and a bottom product II, the distillation being carried out at a bottom temperature of from 100° to 220° C. and from 2 to 15 bar, with the proviso that the pressures in the first and second columns are matched with one another so that a top temperature above 20° C. is obtained at a bottom temperature of not more than 220° C. in each case, (d) the bottom product II containing essentially 6-aminocapronitrile, hexamethylenediamine, adiponitrile, hexamethyleneimine and inert compound A is subjected, in a third column, to a distillation to give the inert compound A as the top product and a bottom product III, the distillation being carried out at a bottom temperature of from 100° to 220° C. and from 0.1 to 2 bar, with the proviso that the inert compound A obtained as the top product is fed to the second column, and, if desired, the distillation being carried out in the presence of a compound B which is inert under the distillation conditions and boils at from 50° to 220° C. at 0.3 bar, (e) the bottom product III containing essentially 6-aminocapronitrile, hexamethylenediamine, adiponitrile, hexamethyleneimine and, if desired, an inert compound B is subjected, in a fourth column, to a distillation to give a top product KP1, containing essentially hexamethyleneimine, if desired inert compound B and hexamethylenediamine, which is obtained at a bottom temperature of from 100° to 220° C. and from 10 to 500 mbar, and a bottom product IV, (f) the top product KP1 is subjected, in a fifth column, to a distillation to give a top product KP2, which contains essentially hexamethyleneimine and, if desired, inert compound B and is obtained at a bottom temperature of from 100° to 220° C. and from 50 to 2000 mbar, and a bottom product V containing essentially hexamethylenediamine in a purity of at least 95%, the top product KP2 being fed to the third column or, if desired, only some of the said top product being fed to the third column and the remainder being discharged, and (g) the bottom product IV containing essentially 6-aminocapronitrile and adiponitrile is subjected, in a sixth column, to a distillation to give 6-aminocapronitrile in a purity of at least 95% as a top product and adiponitrile as the bottom product, the distillation being carried out at a bottom temperature of from 100° to 220° C. and from 1 to 500 mbar, and the 6-aminocapronitrile thus obtained is then cyclized to give caprolactam.

We have also found a process for the simultaneous separation of 6-aminocapronitrile and hexamethylenediamine from a mixture containing these substances.

The partial hydrogenation of adiponitrile can be carried out by one of the known processes, for example by one of the abovementioned processes described in U.S. Pat. No. 4,601,859, U.S. Pat. No. 2,762,835, U.S. Pat. No. 2,208,598, DE-A 848 654, DE-A 954 416, DE-A 4 235 466 or WO 92/21650, in general by hydrogenation in the presence of nickel-, cobalt-, iron- or rhodium-containing catalysts. The catalysts may be used as supported catalysts or as unsupported catalysts. Examples of suitable catalyst carriers are alumina, silica, titanium dioxide, magnesium oxide, active carbon and spinel. Examples of suitable unsupported catalysts are Raney nickel and Raney cobalt.

The catalyst space velocity is usually chosen in the range from 0.05 to 10, preferably from 0.1 to 5, kg of adiponitrile per 1 of catalyst per hour.

The hydrogenation is carried out as a rule at from 20° to 200° C., preferably from 50° to 150° C., and at hydrogen partial pressures of from 0.1 to 20, preferably from 0.5 to 10, MPa.

The hydrogenation is preferably carried out in the presence of a solvent, in particular ammonia. The amount of ammonia is chosen in general to be from 0.1 to 10, preferably from 0.5 to 3, kg of ammonia per kg of adiponitrile.

The molar ratio of 6-aminocapronitrile to hexamethylenediamine and hence the molar ratio of caprolactam to hexamethylenediamine can be controlled by the particular adiponitrile conversion chosen. Adiponitrile conversions from 10 to 80%, preferably from 30 to 60%, are preferably used in order to obtain high 6-aminocapronitrile selectivities.

As a rule, the total amount of 6-aminocapronitrile and hexamethylenediamine is from 95 to 99%, depending on the catalyst and reaction conditions, the most important byproduct in terms of amount being hexamethyleneimine.

In a preferred embodiment, the reaction is carried out in the presence of ammonia and lithium hydroxide, or of a lithium compound which forms lithium hydroxide under the reaction conditions, at from 40° to 120° C., preferably from 50° to 100° C., particularly preferably from 60° to 90° C.; the pressure is chosen in general to be from 2 to 12, preferably from 3 to 10, particularly preferably from 4 to 8, MPa. The residence times are dependent essentially on the desired yield and selectivity and the required conversion; usually, the residence time is chosen so that a maximum yield is obtained, for example in the range from 50 to 275, preferably from 70 to 200, minutes.

The pressure and temperature ranges are preferably chosen so that the reaction can be carried out in a liquid phase.

Ammonia is generally used in an amount such that the ratio of ammonia to dinitrile is from 9:1 to 0.1:1, preferably from 2.3:1 to 0.25:1, particularly preferably from 1.5:1 to 0.4:1.

The amount of lithium hydroxide is chosen as a rule to be from 0.1 to 20, preferably from 1 to 10, % by weight, based on the amount of catalyst used.

Examples of lithium compounds which form lithium hydroxide under the reaction conditions are lithium metal, alkyl- and aryllithium compounds, such as n-butyllithium and phenyllithium. The amount of these compounds is chosen in general so that the above-mentioned amount of lithium hydroxide is obtained.

Nickel-, ruthenium-, rhodium- and cobalt-containing compounds, preferably those of the Raney type, in particular Raney nickel and Raney cobalt, are preferably used as catalysts. The catalysts may also be used in the form of supported catalysts, carriers which may be used being, for example, alumina, silica, zinc oxide, active carbon or titanium dioxide (cf. Appl. Het. Cat. 1987, 106–122; Catalysis 4 (1981), 1–30). Raney nickel (for example from BASF AG, Degussa and Grace) is particularly preferred.

The nickel, ruthenium, rhodium and cobalt catalysts may be modified with metals of group VIB (Cr, Mo or W) and VIII (Fe, Ru, Os, Co (only in the case of nickel), Rh, Ir, Pd or Pt) of the Periodic Table. Observations to date have shown that the use of, in particular, modified Raney nickel catalysts, for example those modified with chromium and/or iron, leads to higher aminonitrile selectivities. (For preparation, cf. DE-A 2 260 978; Bull. Soc. Chem. 13 (1946), 208).

The amount of catalyst is chosen in general so that the amount of cobalt, ruthenium, rhodium or nickel is from 1 to 50, preferably from 5 to 20, % by weight, based on the amount of dinitrile used. The catalysts can be used in the form of fixed-bed catalysts by the liquid-phase or trickle-bed procedure or, preferably, as suspension catalysts.

In a further preferred embodiment, adiponitrile is partially hydrogenated to 6-aminocapronitrile at elevated temperatures and superatmospheric pressure in the presence of a solvent and of a catalyst, by using a catalyst which (a) contains a compound based on a metal selected from the group consisting of nickel, cobalt, iron, ruthenium and rhodium, (b) from 0.01 to 25, preferably from 0.1 to 5, % by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and (c) from 0 to 5, preferably from 0.1 to 3, % by weight, based on (a), of a compound based on an alkali metal or on an alkaline earth metal, with the proviso that, if a compound based only on ruthenium or rhodium or ruthenium and rhodium or nickel and rhodium is chosen as component (a), the promoter (b) can, if desired, be dispensed with.

Preferred catalysts are those in which the component (a) contains at least one compound based on a metal selected from the group consisting of nickel, cobalt and iron, in an amount of from 10 to 95% by weight, and ruthenium and/or rhodium in an amount of from 0.1 to 5% by weight, based in each case on the sum of the components (a) to (c), the component (b) contains at least one promoter based on a metal selected from the group consisting of silver, copper, manganese, rhenium, lead and phosphorus, in an amount of from 0.1 to 5% by weight, based on (a), and the component (c) contains at least one compound based on the alkali metals and alkaline earth metals, selected from the group consisting of lithium, sodium, potassium, cesium, magnesium and calcium, in an amount of from 0.1 to 5% by weight.

Particularly preferred catalysts are:

catalyst A, containing 90% by weight of cobalt oxide (CoO), 5% by weight of manganese oxide ($Mn_2O_3$), 3% by weight of phosphorus pentoxide and 2% by weight of sodium oxide ($Na_2O$), catalyst B, containing 20% by weight of cobalt oxide (CoO), 5% by weight of manganese oxide ($Mn_2O_3$), 0.3% by weight of silver oxide ($Ag_2O$), 70% by weight of silica ($SiO_2$), 3.5% by weight of alumina ($Al_2O_3$), 0.4% by weight of iron oxide ($Fe_2O_3$), 0.4% by weight of magnesium oxide (MgO) and 0.4% by weight of calcium oxide (CaO), and catalyst C, containing 20% by weight of nickel oxide (NiO), 67.42% by weight of silica ($SiO_2$), 3.7% by weight of alumina ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and 2.0% by weight of potassium oxide ($K_2O$).

Preferred catalysts may be unsupported or supported catalysts. Examples of suitable supported catalysts are porous oxides, such as alumina, silica, aluminosilicates, lanthanum oxide, titanium dioxide, zirconium dioxide, magnesium oxide, zinc oxide and zeolites, as well as active carbon or mixtures thereof.

The preparation is carried out as a rule by precipitating precursors of the components (a) together with precursors of the promoters (components (b) and, if desired, with precursors of the trace components (c) in the presence or absence of carrier materials (depending on the catalyst type desired), if desired processing the catalyst precursor thus obtained to give extrudates or tablets, drying the product and then calcining it. Supported catalysts are in general also obtained by impregnating the carrier with a solution of the components (a), (b) and, if desired, (c), it being possible to add the individual components simultaneously or in succession, or by spraying the components (a), (b) and, if desired, (c) onto the carrier by a method known per se.

Suitable precursors of the components (a) are as a rule readily water-soluble salts of the abovementioned metals, such as nitrates, chlorides, acetates, formates and sulfates, preferably nitrates.

Suitable precursors of the components (b) are as a rule readily water-soluble salts or complex salts of the abovementioned metals such as nitrates, chlorides, acetates, formates and sulfates and in particular hexachloroplatinate, preferably nitrates and hexachloroplatinate.

Suitable precursors of the components (c) are as a rule readily water-soluble salts of the abovementioned alkali metals and alkaline earth metals, such as hydroxides, carbonates, nitrates, chlorides, acetates, formates and sulfates, preferably hydroxides and carbonates.

The precipitation is carried out in general from aqueous solutions, either by adding precipitating reagents, by changing the pH or by changing the temperature.

The initial catalyst material thus obtained is usually dried, in general at from 80° to 150° C., preferably from 80° to 120° C.

Calcination is usually carried out at from 150° to 500° C., preferably from 200° to 450° C., in a gas stream comprising air or nitrogen.

After the calcination, the catalyst material obtained is in general exposed to a reducing atmosphere (activation), for example to a hydrogen atmosphere or a gas mixture containing hydrogen and an inert gas, such as nitrogen, for from 2 to 24 hours at from 80° to 250° C., preferably from 80° to 180° C., in the case of catalysts based on ruthenium or rhodium as component (a), or at from 200° to 500° C., preferably from 250° to 400° C., in the case of catalysts based on a metal selected from the group consisting of nickel, cobalt and iron as component (a). The catalyst space velocity here is preferably 200 l per l of catalyst.

The catalyst is advantageously activated directly in a synthesis reactor, since this usually dispenses with an intermediate step which is otherwise required, ie. passivation of the surface at, usually, from 20° to 80° C., preferably from 25° to 35° C., by means of an oxygen/nitrogen mixture, such as air. The activation of passivated catalysts is then preferably carried out in the synthesis reactor at from 180° to 500° C., preferably from 200° to 350° C., in a hydrogen-containing atmosphere.

The catalysts may be used in the form of fixed-bed catalysts by the liquid-phase or trickle-bed procedure or as suspension catalysts.

If the reaction is carried out in a suspension, temperatures of from 40° to 150° C., preferably from 50° to 100° C., particularly preferably from 60° to 90° C., are usually chosen; the pressure is chosen in general to be from 2 to 20, preferably from 3 to 10, particularly preferably from 4 to 9, MPa. The residence times are essentially dependent on the desired yield and selectivity and the required conversion; the residence time is usually chosen so that the maximum yield is obtained, for example in the range from 50 to 275, preferably from 70 to 200, minutes.

In the suspension procedure, the solvents used are preferably ammonia, amines, diamines and triamines of 1 to 6 carbon atoms, such as trimethylamine, triethylamine, tripropylamine and tributylamine, or alcohols, in particular methanol and ethanol, particularly preferably ammonia. A dinitrile concentration of from 10 to 90, preferably from 30 to 80, particularly preferably from 40 to 70, % by weight, based on the sum of dinitrile and solvent, is advantageously chosen.

The amount of catalyst is chosen in general to be from 1 to 50, preferably from 5 to 20, % by weight, based on the amount of dinitrile used.

The hydrogenation in suspension can be carried out batchwise or, preferably, continuously, as a rule in the liquid phase.

The partial hydrogenation may also be carried out batchwise or continuously in a fixed-bed reactor by the trickle-bed or liquid-phase procedure, a temperature of from 20° to 150° C., preferably from 30° to 90° C., and a pressure of, as a rule, from 2 to 30, preferably from 3 to 20, MPa usually being chosen. The partial hydrogenation is preferably effected in the presence of a solvent, preferably ammonia, amines, diamines and triamines of 1 to 6 carbon atoms, such as trimethylamine, triethylamine, tripropylamine and tributylamine, or alcohols, preferably methanol and ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile per l per hour is preferably chosen. Here too, the conversion and hence the selectivity can be controlled by changing the residence time.

BRIEF DESCRIPTION OF THE DRAWING

The drawing represents a flow diagram of the steps of the process.

The partial hydrogenation can be carried out in a conventional reactor suitable for this purpose (R1 in the drawing).

The distillation in the first column (stage (b); K1 in the drawing) is carried out, according to the invention, in such a way that the mixture from stage (a), containing essentially 6-aminocapronitrile, hexamethylenediamine, ammonia, adiponitrile and hexamethyleneimine, preferably a mixture containing essentially from 1 to 70, preferably from 5 to 40, % by weight of 6-aminocapronitrile, from 1 to 70, preferably from 5 to 40, % by weight of adiponitrile, from 0.1 to 30, preferably from 0.5 to 20, % by weight of hexamethylenediamine, from 0.01 to 10, preferably from 0.05 to 5, % by weight of hexamethyleneimine and from 5 to 95, preferably from 20 to 85, % by weight of ammonia, is carried out [sic], as a rule in a conventional distillation column, at a bottom temperature of from 60° to 220° C., preferably from 100° to 200° C., and at from 10 to 30, preferably from 12 to 25, bar in the presence of a compound A which is inert under the distillation conditions and boils at from 60° to 220° C. at 18 bar, to give ammonia as the top product and a bottom product I, the ammonia not being completely separated off.

According to the invention, suitable compounds A are substances which are inert under the distillation conditions and have a boiling point of from 60° to 220° C., preferably from 60 to 150° C., at 18 bar. Examples are alkanes, cycloalkanes, aromatics, naphthenes, alcohols, ethers, nitriles and amines having the above-mentioned properties, in particular $C_5$–$C_8$-alkanes and $C_2$–$C_4$-alkanols, particularly preferably n-pentane, cyclohexane, triethylamine, ethanol, acetonitrile, n-hexane, di-n-propyl ether, isopropanol, n-butylamine or benzene, particularly preferably ethanol.

Compound A is usually added in an amount of from 0.1 to 50, preferably from 1 to 10, % by weight, based on the bottom product I.

In stage (c), the bottom product I, containing essentially 6-aminocapronitrile, hexamethylenediamine, adiponitrile, hexamethyleneimine, inert compound A and ammonia, the ammonia content being lower than that of the mixture obtained from stage (a) and used in stage (b), is subjected to a second distillation to give a mixture comprising the inert compound A and ammonia as the top product and a bottom product II, the distillation being carried out at a bottom temperature of from 100° to 220° C., preferably from 140° to 200° C., and at from 2 to 15, preferably from 4 to 12, bar, with the proviso that the pressures in the first column and in the second column (K2 in the drawing) are matched with one another so that a top temperature above 20° C. is obtained at a bottom temperature of not more than 220° C. in each case.

In stage (d), the bottom product II, containing essentially 6-aminocapronitrile, hexamethylenediamine, adiponitrile, hexamethyleneimine and inert compound A, is subjected, in a third column (K3 in the drawing), to a distillation to give the inert compound A as the top product and a bottom product III, the distillation being carried out at a bottom temperature from 100° to 220° C., preferably from 140° to 200° C., and at from 0.1 to 2, preferably from 0.2 to 1, bar, with the proviso that the inert compound A obtained as the top product is fed to the second column, and, if desired, the distillation is carried out in the presence of a compound B which is inert under the distillation conditions and boils at from 50° to 220° C., preferably from 60° to 150° C., at a given pressure of 0.3 bar.

Examples of compound B are alkanes, cycloalkanes, aromatics, naphthenes, alcohols, ethers, nitriles and amines having the abovementioned properties, in particular di-n-butyl ether, valeronitrile, n-octane, cyclooctane, n-hexylamine and hexamethyleneimine, particularly preferably hexamethyleneimine.

In a preferred embodiment, hexamethyleneimine is chosen as compound B or, particularly preferably, no further compound B is added.

Compound B is preferably added in an amount of from 0.1 to 50, preferably from 0.5 to 10, % by weight, based on the bottom product II.

In stage (e), the bottom product III, containing essentially 6-aminocapronitrile, hexamethylenediamine, adiponitrile, hexamethyleneimine and, if desired, inert compound B, is subjected, in a fourth column (K4 in the drawing), to a distillation to give a top product KP1, containing essentially hexamethyleneimine, if desired inert compound B and hexamethylenediamine, which is obtained at a bottom temperature of from 100° to 220° C., preferably from 140° to 200° C. and from 10 to 500, preferably from 40 to 200 mbar, and a bottom product IV.

In stage (f), the top product KP1 is subjected, in a fifth column (K5 in the drawing), to a distillation to give a top product KP2 which contains essentially hexamethyleneimine and, if desired, inert compound B and is obtained at a bottom temperature of from 100° to 220° C., preferably from 140° to 200° C., and from 50 to 2000, preferably from 300 to 1000, mbar, and a bottom product V, containing essentially hexamethylenediamine in a purity of at least 95%, preferably from 99 to 99.9%, top product KP2 being fed to the third column or, preferably, if desired only some of said top product being fed to the third column and the remainder being discharged.

By discharging some of the top product KP2, which consists essentially of hexamethyleneimine and, if desired, compound B, preferably only hexamethyleneimine if no compound B is added or hexamethyleneimine is used as compound B (cf. stage d), concentration of hexamethyleneimine and, if desired, compound B is generally avoided.

In stage (g), the bottom product IV, containing essentially 6-aminocapronitrile and adiponitrile, is subjected, in a sixth column (K6 in the drawing), to a distillation to give 6-aminocapronitrile in a purity of at least 95%, preferably from 99 to 99.9%, as the top product and adiponitrile as the bottom product, the distillation being carried out at a bottom temperature of from 100° to 220° C., preferably from 140° to 200° C., and from 1 to 500, preferably from 5 to 100, mbar.

According to the invention, the 6-aminocapronitrile obtained is converted into caprolactam. This cyclization can be carried out by a known liquid-phase or gas-phase process, for example by a process from U.S. Pat. No. 2,301,964, U.S. Pat. No. 2,357,484, EP-A 150 295 or DE-A 43 19 134, usually by reacting the 6-aminocapronitrile with water in the liquid phase to give caprolactam and ammonia.

In the reaction in the absence of a catalyst, a temperature of from 200° to 375° C. and reaction times of from 10 to 90, preferably from 10 to 30, minutes are chosen. The solvent used is as a rule water, the 6-aminocapronitrile content generally being chosen to be below 30, preferably from 10 to 25, % by weight, based on the water.

In the liquid-phase reaction in the presence of a catalyst, a temperature of from 50° to 330° C., an amount of water of from 1.3 to 50, preferably from 1.3 to 30, mol per mole of 6-aminocapronitrile and a reaction time of from 10 minutes to several hours are usually chosen. When an organic solvent is used, in particular an alcohol, the amount of water is generally chosen to be from 1.3 to 5 mol per mole of 6-aminocapronitrile.

The reacted mixture obtained in the cyclization is usually worked up initially by distillation, ammonia, water and, if desired, organic solvent being separated off. The catalyst, if used, is present in the bottom product and as a rule is separated from the caprolactam by one of the conventional methods and is recycled to the cyclization reactor (R2 in the drawing). The crude caprolactam is generally converted into pure lactam by purification operations known per se, such as distillation, and the pure lactam is then available for polymerization to polycaprolactam.

In a preferred embodiment, 6-aminocapronitrile is reacted with water in the liquid phase using a heterogeneous catalyst.

The reaction is carried out in the liquid phase at in general from 140° to 320° C., preferably from 160° to 280° C.; the pressure is in general from 1 to 250, preferably from 5 to 150, bar, it being necessary to ensure that the reaction mixture is predominantly liquid under the conditions used. The residence times are in general from 1 to 120, preferably from 1 to 90, in particular from 1 to 60, minutes. In some cases, residence times of from 1 to 10 minutes have proven completely sufficient.

In general, at least 0.01, preferably from 0.1 to 20, in particular from 1 to 5, mol of water are used per mole of 6-aminocapronitrile.

Advantageously, the 6-aminocapronitrile is used in the form of a 1–50, in particular 5–50, particularly preferably 5–30, % strength by weight solution in water (in which case the solvent is simultaneously a reactant) or in a water/solvent mixture. Examples of solvents are alkanols, such as methanol, ethanol, n-propanol, isopropanol, n-butanol, isobutanol and tert-butanol, polyols, such as diethylene glycol and tetraethylene glycol, hydrocarbons, such as petroleum ether, benzene, toluene and xylene, lactams, such as pyrrolidone and caprolactam, and alkyl-substituted lactams, such as N-methylpyrrolidone; N-methylcaprolactam and N-ethylcaprolactam, and carboxylates, preferably of carboxylic acids of 1 to 8 carbon atoms. Ammonia may also be present in the reaction. Mixtures of organic solvents may of course also be used. Mixtures of water and alkanols in a water/alkanol weight ratio of 1–75/25–99, preferably 1–50/50–99, have proven particularly advantageous in some cases.

It is in principle also possible to use 6-aminocapronitrile as a reactant and simultaneously as a solvent.

Examples of heterogeneous catalysts which may be used are acidic, basic or amphoteric oxides of the elements of the second, third or fourth main group of the Periodic Table, such as calcium oxide, magnesium oxide, boron oxide, alumina, tin oxide or silica in the form of pyrogenic silica, silica gel, kieselguhr, quartz or mixtures thereof, and oxides of metals of the second to sixth subgroups of the Periodic Table, such as titanium oxide, amorphous or as anatase or rutile, zirconium oxide, zinc oxide, manganese oxide or mixtures thereof. Oxides of the lanthanides and actinides, such as cerium oxide, thorium oxide, praseodymium oxide, samarium oxide, rare earth mixed oxides or mixtures thereof with the abovementioned oxides may also be used. Examples of further catalysts may be:

vanadium oxide, niobium oxide, iron oxide, chromium oxide, molybdenum oxide, tungsten oxide or mixtures thereof. Mixtures of the stated oxides with one another are also possible. Some sulfides, selenides and tellurides, such as zinc telluride, tin selenide, molybdenum sulfide, tungsten sulfide and sulfides of nickel, zinc and chromium may also be used.

The abovementioned compounds may be doped with compounds of the 1st and 7th main groups of the Periodic Table or may contain these compounds.

Zeolites, phosphates and heteropolyacids and acidic and alkaline ion exchangers, for example Naphion®, are further suitable catalysts.

If required, these catalysts may contain up to 50% by weight of copper, tin, zinc, manganese, iron, cobalt, nickel, ruthenium, palladium, platinum, silver or rhodium.

Depending on the composition of the catalyst, it may be used as an unsupported catalyst or supported catalyst. For example, titanium dioxide can be used as titanium dioxide extrudates or as titanium dioxide applied in a thin layer on a carrier. All methods described in the literature may be used for applying titanium dioxide to a carrier, such as silica, alumina or zirconium dioxide. Thus, a thin titanium dioxide layer can be applied by hydrolysis of titanium organyls, such as titanium isopropylate or titanium butylate, or by hydrolysis of $TiCl_4$ or other inorganic titanium-containing compounds. Sols containing titanium dioxide may also be used.

Further suitable compounds are zirconyl chloride, aluminum nitrate and cerium nitrate.

Suitable carriers are powders, extrudates or pellets of the stated oxides themselves or of other stable oxides, such as silica. The carriers used may be rendered macroporous in order to improve the mass transport.

In a further preferred embodiment, 6-aminocapronitrile is cyclized in the liquid phase with water at elevated temperatures in the absence of a catalyst by heating an aqueous solution of 6-aminocapronitrile in the liquid phase without the addition of a catalyst in a reactor to give a mixture I consisting essentially of water, caprolactam and a high-boiling fraction (high boiler). In this preferred embodiment, water is preferably used in excess, particularly preferably from 10 to 150, in particular from 20 to 100, mol of water being used per mole of 6-aminocapronitrile and an aqueous solution of 6-aminocapronitrile being obtained. In a further preferred embodiment, from 5 to 25 mol of water are usually used per mole of 6-aminocapronitrile, and the solution can in general be further diluted to 5–25% by weight of 6-aminocapronitrile by adding an organic solvent.

Examples of suitable solvents are:

$C_1$–$C_4$-alkanols, such as methanol, ethanol, n-propanol, isopropanol and butanols, glycols such as ethylene glycol, diethylene glycol, triethylene glycol and tetraethylene glycol, ethers, such as methyl tert-butyl ether and diethylene glycol diethyl ether, $C_6$–$C_{10}$-alkanes, such as n-hexane, n-heptane, n-octane, n-nonane and n-decane, and cyclohexane, benzene, toluene, xylene, lactams, such as pyrrolidone and caprolactam, and N—$C_1$–$C_4$-alkyllactams, such as N-methylpyrrolidone, N-methylcaprolactam and N-ethylcaprolactam.

In a further embodiment, from 0 to 5, preferably from 0.1 to 2, % by weight of ammonia, hydrogen or nitrogen may be added to the reaction mixture.

The reaction is preferably carried out at from 200° to 370° C., preferably from 220° to 350° C., particularly preferably from 240° to 320° C.

The reaction is usually carried out under superatmospheric pressure, the pressure as a rule being chosen in the range from 0.1 to 50, preferably from 5 to 25, MPa, so that the reaction mixture is preferably present as a liquid phase.

The duration of the reaction depends essentially on the process parameters chosen and is in general from 20 to 180 and preferably from 20 to 90, minutes in the continuous process. As a rule, the conversion decreases in the case of shorter reaction times, and observations to date have shown that troublesome oligomers form in the case of longer reaction times.

The cyclization is preferably carried out continuously, preferably in a tube reactor, a stirred kettle or a combination thereof.

The cyclization can also be carried out batchwise. The reaction then usually takes from 30 to 180 minutes.

As a rule, the discharged mixture consists essentially of from 50 to 98, preferably from 80 to 95, % by weight of water and from 2 to 50, preferably from 5 to 20, % by weight of a mixture comprising essentially from 50 to 90, preferably from 65 to 85, % by weight of caprolactam and from 10 to 50, preferably from 15 to 35, % by weight of a high-boiling fraction (high boiler).

In a preferred embodiment, any abraded catalyst material and non-volatile high boilers present after the partial hydrogenation and after ammonia and inert compound A (bottom product of column 3) have been separated off are removed by evaporation by the undesirable substances being obtained as a bottom product.

In a further preferred embodiment, adiponitrile is separated off by distillation from the bottom product of column 6, containing adiponitrile and high boilers, and is fed to stage (a). It is also possible to discharge a bleed stream from the bottom of column 6.

In a further embodiment, bottom product III can be fed to a fourth column, the distillation being carried out in such a way that a top product comprising hexamethyleneimine and, if desired, compound B, and a bottom product IV' are obtained. Some of the top product is recycled to column III and the remainder is discharged in order to avoid concentration.

The bottom product IV' is fed to a fifth column, distillation being effected under conditions such that a top product comprising hexamethylenediamine and a bottom product V' are obtained. This bottom product V' is fed to a sixth column to give 6-aminocapronitrile as a top product and adiponitrile as the bottom product.

The distillation in the fourth column of the last mentioned embodiment is preferably carried out at a bottom temperature of from 100° to 220° C., preferably from 140° to 200° C., and at from 50 to 2000, preferably from 300 to 1000, mbar.

The distillation in the fifth column of the last mentioned embodiment is preferably carried out at a bottom temperature of from 100° to 220° C., preferably from 140° to 200° C., and at from 10 to 500, preferably from 40 to 200, mbar.

The distillation in the sixth column of the last mentioned embodiment is preferably carried out at a bottom temperature of from 100° to 220° C., preferably from 140° to 200° C., and at from 1 to 500, preferably from 5 to 100, mbar.

The further processing of the products hexamethylenediamine, 6-aminocapronitrile and adiponitrile obtained in this preferred embodiment is advantageously carried out similarly to the novel process.

In a further preferred embodiment, high boilers are removed from the bottom product III by distillation before said bottom product is fed to the fourth column. Any separation of high boilers from the bottom product of column 6, containing adiponitrile, can thus be dispensed with.

The hexamethylenediamine obtained according to the invention can be further purified by conventional methods and used for the preparation of polymers and copolymers, such as polyamide 66.

According to the invention, part of the process for the preparation of caprolactam from adiponitrile can also be used for the simultaneous separation of 6-aminocapronitrile and hexamethylenediamine by distillation of a mixture containing essentially these compounds, by a process in which (a) a mixture containing essentially 6-aminocapronitrile, hexamethylenediamine, ammonia, adiponitrile and hexamethyleneimine is subjected to a distillation to give ammonia as the top product and a bottom product I, the distillation being carried out at a bottom temperature of from 60° to 220° C. and at from 10 to 30 bar in the presence of a compound A which is inert under the distillation conditions and boils at from 60° to 220° C. at 18 bar, and the ammonia not being completely separated off, (b) the bottom product I, containing essentially 6-aminocapronitrile, hexamethylenediamine, adiponitrile, hexamethyleneimine, inert compound A and ammonia, the ammonia content being lower than that of the mixture used in stage (a), is subjected to a second distillation to give a mixture comprising the inert compound A and ammonia as the top product and a bottom product II, the distillation being carried out at a bottom temperature of from 100° to 220° C. and at from 2 to 15 bar, with the proviso that the pressures in the first and in the second columns are matched with one another so that a top temperature above 20° C. is obtained at a bottom temperature of not more than 220° C. in each case, (c) the bottom product II, containing essentially 6-aminocapronitrile, hexamethylenediamine, adiponitrile, hexamethyleneimine, and inert compound A, is subjected, [lacuna] a third column, to a distillation to give the inert compound A as the top product and a bottom product III, the distillation being carried out at a bottom temperature of from 100° to 220° C. and at from 0.1 to 2 bar, with the proviso that the inert compound A obtained as the top product is fed to the second column and, if desired, the distillation is carried out in the presence of a compound B which is inert under the distillation conditions and boils at from 50° to 220° C. at 0.3 bar, (d) the bottom product III, containing essentially 6-aminocapronitrile, hexamethylenediamine, adiponitrile, hexamethyleneimine and, if desired, an inert compound B, is subjected, in a fourth column, to a distillation to give a top product KP1, containing essentially hexamethyleneimine, if desired inert compound B and hexamethylenediamine, which is obtained at a bottom temperature of from 100° to 220° C. and at from 10 to 500 bar, and a bottom product IV, (e) the top product KP1 is subjected, in a fifth column, to a distillation to give a top product KP2 which contains essentially hexamethyleneimine and, if desired, inert compound B and is obtained at a bottom temperature of from 100° to 220° C. and at from 50 to 2000 mbar, and a bottom product V, containing essentially hexamethylenediamine in a purity of at least 95%, the top product KP2 being fed to the third column or, if required, at least some of said top product being fed to the third column and the remainder being discharged, and (f) the bottom product IV, containing essentially 6-aminocapronitrile and adiponitrile, is subjected, in a sixth column, to a distillation to give 6-aminocapronitrile in a purity of at least 95% as the top product and adiponitrile as the bottom product, the distillation being carried out at a bottom temperature of from 100° to 220° C. and at from 1 to 500 mbar.

The novel process has the advantage that a continuous process for the preparation of caprolactam, simultaneously obtaining hexamethylenediamine, is possible starting from adiponitrile.

EXAMPLES

Example 1

(a) Hydrogenation of Adiponitrile to 6-aminocapronitrile

A mixture of 4.6 kg of adiponitrile (ADN), 4.6 kg of ammonia, 0.45 kg of suspended Raney nickel (H 1–50;

BASF) and 8 g of lithium hydroxide was hydrogenated at 80° C. and at a total pressure of 70 bar for 1 hour in a stirred autoclave ($H_2$ partial pressure=40 bar).

After the Raney nickel had been separated off, the discharged hydrogenation mixture had the following composition: 2.5 kg of ADN, 2 kg of 6-aminocapronitrile (ACN), 0.2 kg of hexamethylenediamine (HMD), 10 g of hexamethyleneimine (HMI) and 4.5 kg of ammonia.

(b) Working up the Discharged Hydrogenation Mixture by Distillation

The discharged hydrogenation mixture obtained from (a) and freed from the catalyst was fed to the top of a first column having two theoretical plates. 4.5 kg of ammonia containing 200 ppm of ACN were separated off via the top at 47° C. and 19 bar and were used for the hydrogenation (stage (a)).

The bottom product of the first column, a reaction mixture containing ethanol and small amounts of ammonia, was fed, at a bottom temperature of 180° C., into a second column having 13 theoretical plates.

0.4 kg of a mixture of 25% by weight of ammonia and 75% by weight of ethanol was recycled from the top of this column at 50° C. and 10 bar to the first column.

The bottom product of the second column, which contained 30% by weight of ethanol and 30 ppm of ammonia and was at 180° C., was fed to a third column having 14 theoretical plates. 2 kg of ethanol were removed via the top of this column at 50° C./300 mbar and recycled to the second column.

4.8 kg of product having a hexamethyleneimine (HMI) content of 2% by weight were removed from the bottom of the third column, which was at 180° C., and fed to a fourth column having 20 theoretical plates. 0.3 kg of product containing 65% by weight of HMD, 35% by weight of HMI and 1000 ppm of ACN was removed via the top of this column at 90° C./85 mbar.

The top product removed from the fourth column was fed to a fifth column having 15 theoretical plates. At 114° C./500 mbar, 90 g of HMI containing 1000 ppm of HMD were removed as the top product and recycled to the third column. 190 g of HMD containing 100 ppm of HMI were taken off from the bottom of the column at 177° C. and removed from the process.

The bottom product removed from the fourth column was fed to a sixth column having 15 theoretical plates. 2 kg of ACN containing 1000 ppm of HMD and 100 ppm of ADN were taken off via the top of this column at 111° C./15 mbar and discharged. 2.5 kg of ADN containing 500 ppm of ACN were discharged via the bottom.

(c) Cyclization of 6-aminocapronitrile to Caprolactam

A solution of 2 kg of ACN (from (b)), 0.64 kg of water and 17.4 kg of ethanol was passed, at 230° C. and 80 bar in a residence time of 15 minutes, through an oil-heated tube reactor filled with 4 mm titanium dioxide extrudates and having a length/diameter ratio of 100. The discharged reaction mixture contained 1.8 kg of caprolactam, 0.05 kg of ethyl 6-aminocaproate, 0.04 kg of 6-aminocapronitrile (determined by gas chromatography) and 0.11 kg of 6-aminocaproic acid and oligomers and polymers of caprolactam (determined by HPLC). 1.7 kg of caprolactam were obtained therefrom by fractional distillation.

Example 2

(a) Hydrogenation of Adiponitrile to 6-aminocapronitrile

A tube reactor (length: 2 m, inner diameter: 2.5 cm) filled with 750 ml (1534 g) of a catalyst, consisting of CoO (90% by weight), $Mn_2O_3$ (5% b.w.), $P_2O_5$ (3% b.w.), and $Na_2O$ (2% b.w.) was heated within 48 h to a temperature of 280° C. in a stream of hydrogen (500 l/h) at atmospheric pressure. Thereafter the temperature was lowered to 42° C. (entrance), resp. 80° C. (exit).

Then a mixture of 380 g/h adiponitrile, 380 g/h ammonia and 500 l/h hydrogen were added to this reactor at a total pressure of 200 bar. The discharged hydrogenation mixture was collected, and (after having reached steady state) 3 kg/h of this mixture was continuously added to the starting mixture. With this measure, approximately four times the amount of fresh starting mixture was recycled.

The adiponitrile conversion was 60%. The discharged hydrogenation mixture had the following composition: 50% b.w. ammonia, 20% b.w. adiponitrile, 18% b.w. 6-aminocapronitrile, 11.9% b.w. hexamethylene diamine, 0.05% b.w. hexamethyleneimine and 0.05% b.w. others (mainly high boilers). ACN-selectivity: 60% (ACN+HMD) -selectivity: >99%.

(b) Working up the Discharged Hydrogenation Mixture by Distillation 10 kg of the discharged hydrogenation mixture obtained from ex. 2 (a) was fed to the top of a first column having two theoretical plates. 5.0 kg of ammonia containing 20 ppm of ACN were separated off via the top at 47° C. and 19 bar and were used for the hydrogenation (stage (a)).

The bottom product of the first column, a reaction mixture containing ethanol and small amounts of ammonia, was fed, at a bottom temperature of 180° C., into a second column having 10 theoretical plates.

1.2 kg of a mixture of 30% by weight of ammonia and 70% by weight of ethanol was recycled from the top of this column at 50° C. and 10 bar to the first column.

The bottom product of the second column, which contained 40% by weight of ethanol and 90 ppm of ammonia and was at 177° C., was fed to a third column having 10 theoretical plates. 3.2 kg of ethanol were removed via the top of this column at 47° C./300 mbar and recycled to the second column.

5 kg of product having a hexamethyleneimine (HMI content of 0.55% by weight were removed from the bottom of the third column, which was at 180° C., and fed to a fourth column having 20 theoretical plates. 1.22 kg of product containing 97.8% by weight of HMD, 2.2% by weight of HMI and 1000 ppm of ACN was removed via the top of this column at 90° C./85 mbar.

The top product removed from the fourth column was fed to a fifth column having 15 theoretical plates. At 114° C./500 mbar, 26 g of HMI containing 1000 ppm of HMD were removed as the top product and 22 g of this removed HMI were recycled to the third column. 1190 g of HMD containing 100 ppm of HMI were taken off from the bottom of the column at 177° C. and removed from the process.

The bottom product removed from the fourth column was fed to a sixth column having 15 theoretical plates. 1.8 kg of ACN containing 1000 ppm of HMD and 100 ppm of ADN were taken off via the top of this column at 111° C./15 mbar and discharged. 2.0 kg of ADN containing 500 ppm of ACN were discharged via the bottom.

(c) Cyclization of 6-aminocapronitrile to Caprolactam

A solution of 2 kg of ACN (from ex. 2(b)), 0.64 kg of water and 17.4 kg of ethanol was passed, at 230° C. and 80 bar in a residence time of 15 minutes, through an oil-heated tube reactor filled with 4 mm titanium dioxide extrudates and having a length/diameter ratio of 100. The discharged reaction mixture contained 1.8 kg of caprolactam, 0.05 kg of ethyl 6-aminocaproate, 0.04 kg of 6-aminocapronitrile (determined by gas chromatography) and 0.11 kg of 6-aminocaproic acid and oligomers and polymers of caprolactam (determined by HPLC). 1.7 kg of caprolactam were obtained therefrom by fractional distillation.

We claim:

1. A process for the simultaneous preparation of caprolactam and hexamethylenediamine starting from adiponitrile, wherein (a) adiponitrile is partially hydrogenated to give a mixture containing essentially 6-aminocapronitrile, hexamethylenediamine, ammonia, adiponitrile and hexamethyleneimine, (b) the mixture obtained in (a) is subjected to a distillation to give ammonia as the top product and a bottom product I, the distillation being carried out at a bottom temperature of from 60° to 220° C. and a pressure of from 10 to 30 bar in the presence of a compound A which is inert under the distillation conditions and boils at from 60° to 220° C. at 18 bar, and the ammonia not being completely separated off, (c) the bottom product I containing essentially 6-aminocapronitrile, hexamethylenediamine, adiponitrile, hexamethyleneimine, inert compound A and ammonia, the ammonia content being lower than that of the mixture used in stage (b), is subjected to a second distillation to give a mixture comprising the inert compound A and ammonia as the top product and a bottom product II, the distillation being carried out at a bottom temperature of from 100° to 220° C. and from 2 to 15 bar, with the proviso that the pressures in the first and second columns are matched with one another so that a top temperature above 20° C. is obtained at a bottom temperature of not more than 220° C. in each case, (d) the bottom product II containing essentially 6-aminocapronitrile, hexamethylenediamine, adiponitrile, hexamethyleneimine and inert compound A is subjected, in a third column, to a distillation to give the inert compound A as the top product and a bottom product III, the distillation being carried out at a bottom temperature of from 100° to 220° C. and from 0.1 to 2 bar, with the proviso that the inert compound A obtained as the top product is fed to the second column, and, if desired, the distillation being carried out in the presence of a compound B which is inert under the distillation conditions and boils at from 50° to 220° C. at 0.3 bar, (e) the bottom product III containing essentially 6-aminocapronitrile, hexamethylenediamine, adiponitrile, hexamethyleneimine and, if desired, an inert compound B is subjected, in a fourth column, to a distillation to give a top product KP1, containing essentially hexamethyleneimine, if desired inert compound B and hexamethylenediamine, which is obtained at a bottom temperature of from 100° to 220° C. and from 10 to 500 mbar, and a bottom product IV, (f) the top product KP1 is subjected, in a fifth column, to a distillation to give a top product KP2, which contains essentially hexamethyleneimine and, if desired, inert compound B and is obtained at a bottom temperature of from 100° to 220° C. and from 50 to 2000 mbar, and a bottom product V containing essentially hexamethylenediamine in a purity of at least 95%, the top product KP2 being fed to the third column or, if desired, only some of the said top product being fed to the third column and the remainder being discharged, and (g) the bottom product IV containing essentially 6-aminocapronitrile and adiponitrile is subjected, in a sixth column, to a distillation to give 6-aminocapronitrile in a purity of at least 95% as a top product and adiponitrile as the bottom product, the distillation being carried out at a bottom temperature of from 100° to 220° C. and from 1 to 500 mbar, and the 6-aminocapronitrile thus obtained is then cyclized to give caprolactam.

2. A process as claimed in claim 1, wherein adiponitrile is separated off by distillation from the bottom product of column 6, containing adiponitrile and high boilers, and is fed to stage (a).

3. A process for the simultaneous separation of 6-aminocapronitrile and hexamethylenediamine by distillation of a mixture containing essentially these compounds, wherein (a) a mixture containing essentially 6-aminocapronitrile, hexamethylenediamine, ammonia, adiponitrile and hexamethyleneimine is subjected to a distillation to give ammonia as the top product and a bottom product I, the distillation being carried out at a bottom temperature of from 60° to 220° C. and at from 10 to 30 bar in the presence of a compound A which is inert under the distillation conditions and boils at from 60° to 220° C. at 18 bar, and the ammonia not being completely separated off, (b) the bottom product I, containing essentially 6-aminocapronitrile, hexamethylenediamine, adiponitrile, hexamethyleneimine, inert compound A and ammonia, the ammonia content being lower than that of the mixture used in stage (a), is subjected to a second distillation to give a mixture comprising the inert compound A and ammonia as the top product and a bottom product II, the distillation being carried out at a bottom temperature of from 100° to 220° C. and at from 2 to 15 bar, with the proviso that the pressures in the first and in the second columns are matched with one another so that a top temperature above 20° C. is obtained at a bottom temperature of not more than 220° C. in each case, (c) the bottom product II, containing essentially 6-aminocapronitrile, hexamethylenediamine, adiponitrile, hexamethyleneimine, and inert compound A, is subjected, a third column, to a distillation to give the inert compound A as the top product and a bottom product III, the distillation being carried out at a bottom temperature of from 100° to 220° C. and at from 0.1 to 2 bar, with the proviso that the inert compound A obtained as the top product is fed to the second column and, if desired, the distillation is carried out in the presence of a compound B which is inert under the distillation conditions and boils at from 50° to 220° C. at 0.3 bar, (d) the bottom product III, containing essentially 6-aminocapronitrile, hexamethylenediamine, adiponitrile, hexamethyleneimine and, if desired, an inert compound B, is subjected, in a fourth column, to a distillation to give a top product KP1, containing essentially hexamethyleneimine, if desired inert compound B and hexamethylenediamine, which is obtained at a bottom temperature of from 100° to 220° C. and at from 10 to 500 bar, and a bottom product IV, (e) the top product KP1 is subjected, in a fifth column, to a distillation to give a top product KP2 which contains essentially hexamethyleneimine and, if desired, inert compound B and is obtained at a bottom temperature of from 100° to 220° C. and at from 50 to 2000 mbar, and a bottom product V, containing essentially hexamethylenediamine in a purity of at least 95%, some of the top product KP2 being fed to the third column or, if required, at least some of said top product being fed to the third column and the remainder being discharged, and (f) the bottom product IV, containing essentially 6-aminocapronitrile and adiponitrile, is subjected, in a sixth column, to a distillation to give 6-aminocapronitrile in a purity of at least 95% as the top product and adiponitrile as the bottom product, the distillation being carried out at a bottom temperature of from 100° to 220° C. and at from 1 to 500 mbar.

4. A process as claimed in claim 1, wherein a mixture consisting essentially of from 1 to 70% by weight of 6-aminocapronitrile,
from 1 to 70% by weight of adiponitrile,
from 0.1 to 30% by weight of hexamethylenediamine,
from 0.01 to 10% by weight of hexamethyleneimine and
from 5 to 95% by weight of ammonia is used in stage (b).

5. A process as claimed in claim 3, wherein a mixture consisting essentially of from 1 to 70% by weight of 6-aminocapronitrile,
from 1 to 70% by weight of adiponitrile,
from 0.1 to 30% by weight of hexamethylenediamine,
from 0.01 to 10% by weight of hexamethyleneimine and
from 5 to 95% by weight of ammonia is used in stage (a).

6. A process as claimed in claim 1, wherein ethanol is used as the inert compound A.

7. A process as claimed in claim 1, wherein hexamethyleneimine is used as component B.

8. A process as claimed in claim 3, wherein ethanol is used as the inert compound A.

9. A process as claimed in claim 3, wherein hexamethyleneimine is used as component B.

* * * * *